United States Patent [19]
Soldner et al.

[11] 4,043,321
[45] Aug. 23, 1977

[54] ARRANGEMENT FOR ULTRASONIC-ECHO ENCEPHALOGRAPHY

[75] Inventors: Richard Soldner, Erlangen; Alfred Walz, Nurnberg, both of Germany

[73] Assignee: Siemens Aktiengesellschaft, Berlin & Munich, Germany

[21] Appl. No.: 559,365

[22] Filed: Mar. 17, 1975

[30] Foreign Application Priority Data

Mar. 25, 1974 Germany .............................. 2414218

[51] Int. Cl.$^2$ .............................................. A61B 10/00
[52] U.S. Cl. ........................................ 128/2 V; 73/67.9
[58] Field of Search ........................ 128/2 V, 2.05 Z; 73/67.7–67.9

[56] References Cited

U.S. PATENT DOCUMENTS

| | | | |
|---|---|---|---|
| 3,323,512 | 6/1967 | Clynes .................... | 128/2 V |
| 3,554,186 | 1/1971 | Leksell et al. ............ | 128/2 V |
| 3,681,977 | 8/1972 | Wendt et al. ............. | 128/2 V X |
| 3,713,329 | 1/1973 | Munger .................... | 128/2 V X |
| 3,872,858 | 3/1975 | Hudson et al. ........... | 128/2 V |

*Primary Examiner*—Kyle L. Howell
*Attorney, Agent, or Firm*—Hill, Gross, Simpson, Van Santen, Steadman, Chiara & Simpson

[57] ABSTRACT

An arrangement for effecting ultrasonic-echo encephalography, including at least two ultrasonic heads, as well as a recording arrangement for the ultrasonic waves which are received from the skull of a patient, and having at least one marking device associated therewith for marking the position of the theoretical median echo. The marking arrangement incorporates a time measurement element for determining the transit time of the ultrasonic wave through the skull portion being examined by means of the sound-penetrating operation which, after switching over to a reflecting operation, so controls an impulse generator in that the latter, periodically in beat with the ultrasonic radiation, and delayed with respect to the timepoint of the ultrasonic entry into the skull examination area by the amount of the previously determined skull transit time, as to produce a marking impulse at the recording arrangement.

12 Claims, 2 Drawing Figures

ARRANGEMENT FOR ULTRASONIC-ECHO ENCEPHALOGRAPHY

FIELD OF THE INVENTION

The present invention relates to an arrangement for effecting ultrasonic-echo encephalography, including at least two ultrasonic heads, as well as a recording arrangement for the ultrasonic waves which are received from the skull of a patient, and having at least one marking device associated therewith for marking the position of the theoretical median echo.

DISCUSSION OF THE PRIOR ART

The theoretical median echo of the skull is obtained as known, in that an ultrasonic head is applied to, respectively, both sides of the patient's skull and wherein, during the sound penetrating operation, the currently received ultrasonic signal is temporarily recorded on the recording arrangement, the latter of which is usually an electron-beam oscillograph. In order to maintain this median echo for the subsequent actual ultrasonic-echo measurement, a mechanical or possibly an electronic index mark is manually slid over the echo. This manual adjustment cannot be undertaken by the physician himself, since he requires both of his hands for the application of both ultrasonic heads. Thereby, more frequently an additional assistant is required.

SUMMARY OF THE INVENTION

Accordingly, it is an object of the present invention to provide an arrangement of the above-mentioned type which is so constructed that the fixation of the theoretical median echo which is detected through the through-sounding operation is automatically obtained, meaning, without the aid of an assistant.

The foregoing object is inventively attained in that the marking arrangement incorporates a time measurement element for determining the transit time of the ultrasonic wave through the skull portion being examined by means of the sound-penetrating operation which, after switching over to a reflecting operation, so controls an impulse generator in that the latter, periodically in beat with the ultrasonic radiation, and delayed with respect to the timepoint of the ultrasonic entry into the skull examination area by the amount of the previously determined skull transit time, as to produce a marking impulse at the recording arrangement.

In the apparatus according to the invention, the position of the theoretical median echo during the sound-penetrating process is determined once through an electromechanical ultrasonic-time measurement, and subsequently during reflecting operation, through periodic electronic regeneration, the median echo as the marking impulse is continually retarded by the previous determined transit time, meaning, in correspondence the basic position blended into the echo recordation (ultrasonic-echo encephalograph). Inasmuch as the periodic remarking of the theoretical median echo continues fully automatically, in the present inventive arrangement, the reception of the echo-encephalograph may be carried out by a single person, for example, the physician himself. In contrast to the presently known installation, there is thus no longer a need for an assistant.

BRIEF DESCRIPTION OF THE DRAWINGS

Further advantages and details of the invention may now be ascertained from the following description of an exemplary embodiment thereof, taken in conjunction with the accompanying drawings; in which.

DETAILED DESCRIPTION

Figure 1:
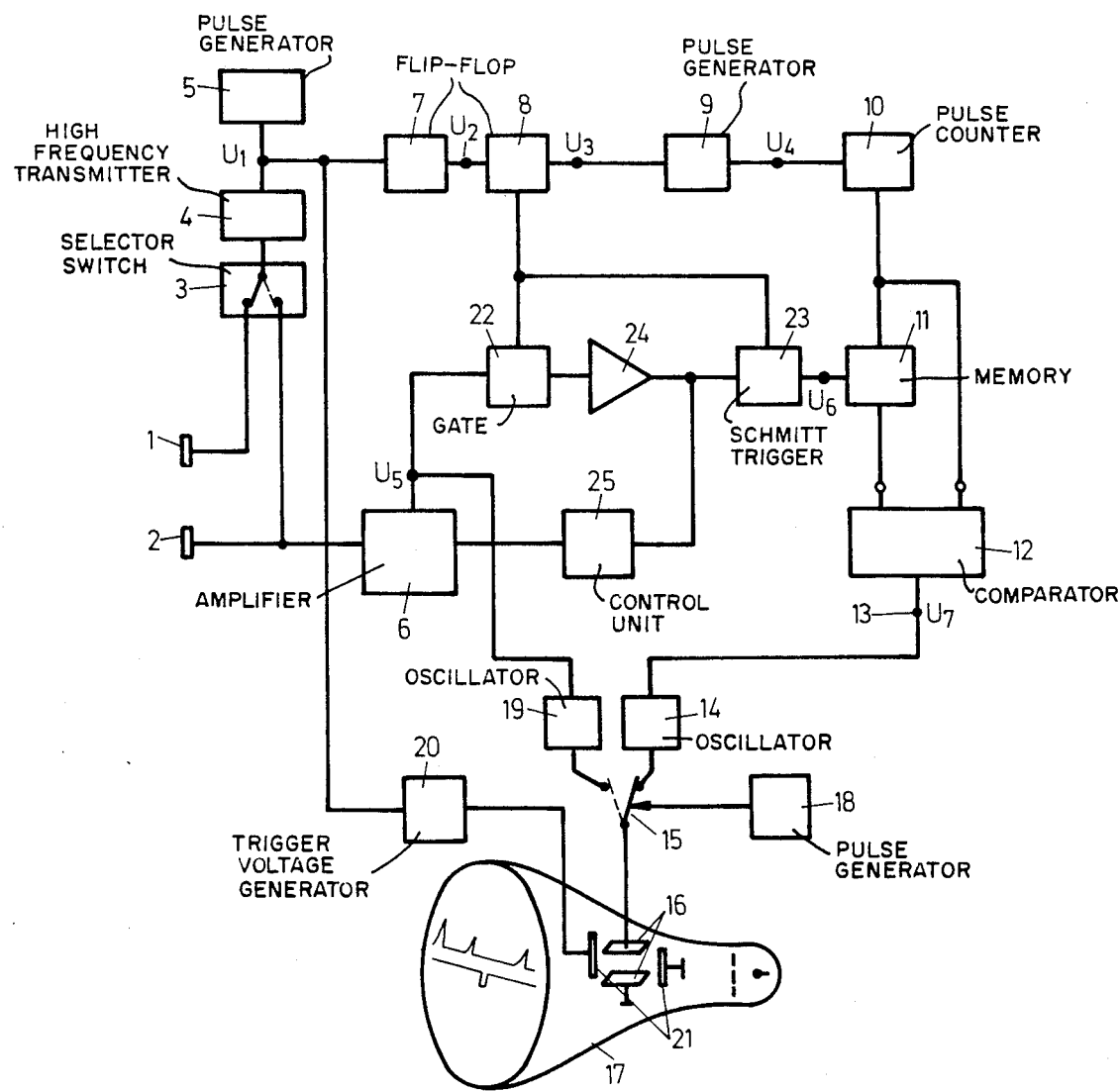
FIG. 1 is a schematic circuit diagram of an arrangement constructed according to the present invention.

Referring to FIG. 1 of the drawings, ultrasonic heads 1 and 2 each include in the usual manner, for example, piezoelectric crystal plates forming ultrasonic vibrators. In the illustrated form, the ultrasonic head 1 alone serves as an ultrasonic transmitter for the sounding measurements. In contrast therewith, the ultrasonic head 2 serves as the ultrasonic receiver for the ultrasonic transmitting sound of head 1 during the sounding measurement, as well as an ultrasonic transmitter and receiver during the subsequent echo measurement for determination of the ultrasonic-echo encephalograph (reflecting operation). The two ultrasonic heads 1 and 2, by means of a selector switch 3 (electronic switch, for example, transistor switch), are hereby individually selectively connectable with a high-frequency transmitter 4 which, in beat with a transmission impulse generator 5 (approximately 0.5 to 2 kHz), transmits high-frequency impulses to the thereto connected first or sound ultrasonic head for effecting the excitation thereof.

Only the second ultrasonic head 2 has an ultrasonic-receiving amplifier 6 connected thereto which, during sounding operation, amplifies the transmitted sound from the head 1 received by this head 2, respectively, at pure reflection operation the echo impulses received by the head 2 after emitting a transmission impulse, as corresponding electrical signals.

Further connected to the transmission pulse generator 5 in series are two monostable flip-flops or triggers 7 and 8. Following these flip-flops is an impulse generator 9 for producing counting impulses (pulse frequency of approximately 2 MHz), as well as an impulse counter 10. Connected to the output of the counter 10 there is again a digital storage or memory 11, preferably a storage flip-flop, for the storing of the counting positions of the counter 10. A digital comparator 12 serves for comparison of the counting conditions of the counter 10, as well as that of the storage 11. At the same position of the two counter conditions, this comparator 12 presently generates at its output 13 an output impulse which is transmissible through a selector switch 15, as well as, upon occasion, through a preceding constant potential oscillator 14, to the paired vertical deflector plates 16 of an electron-beam tube 17. The selector switch 15 is alternatingly switched in rhythm with a pulse generator 18 at a high frequency (in the kHz range) into either the solidly drawn or into phantom illustrated switched positions. In the phantom-illustrated switched position, the paired vertical deflector plates 16 of the electron-beam tube 17 are thereby (eventually through a further constant potential oscillator 19) connected with the signal-output of the ultrasonic-receiving signal amplifier 6. In this switched position of the selector switch 15, accordingly, at a rapid periodic horizontal deflection of the electron beam of the tube in the ultrasonic transmission pulse, by means of the transmission generator respectively impacted trigger voltage generator 20 for the horizontal plates 21 of the electrode beam tube 17 which is contacted by the transmission-pulse impulses of the transmission pulse generator, the ultrasonic signals received by the receiver 6 are illustrated as vertical teeth or ridges on the tube picture screen.

The components 22 and 23 are respectively an electronic gate and a Schmitt-trigger. Designated by reference numeral 24 further is an amplifier for the signals which appear at the output of the gate 22. A control element 25 controls the degree of amplification of receiving amplifier 6 to higher or lower values dependent upon the signals of the receiving amplifier 6, as well as the output signals of the amplifier 24.

The function of the arrangement according to FIG. 1 is now described in greater detail in conjunction with the voltage diagram shown in FIG. 2 of the drawings, as follows:

Preceding the initiation of each exposure of an ultrasonic-echo encephalograph on the picture screen of the electron-beam tube 17, in order to determine the theoretical median echo, the ultrasonic head 1 is positioned at one side of the skull, as well as the ultrasonic head 2 at the opposite side thereof. The apparatus is switched to sounding measurement operation, meaning, that the switch 3 is located in the solidly illustrated switching position. Thereafter, the ultrasonic head periodically transmits ultrasonic impulses in transmitting pulse or rhythm with the transmission pulse generator 5 through the skull in the direction towards the ultrasonic head 2, the latter of which operates as a receiver.

Figure 2:
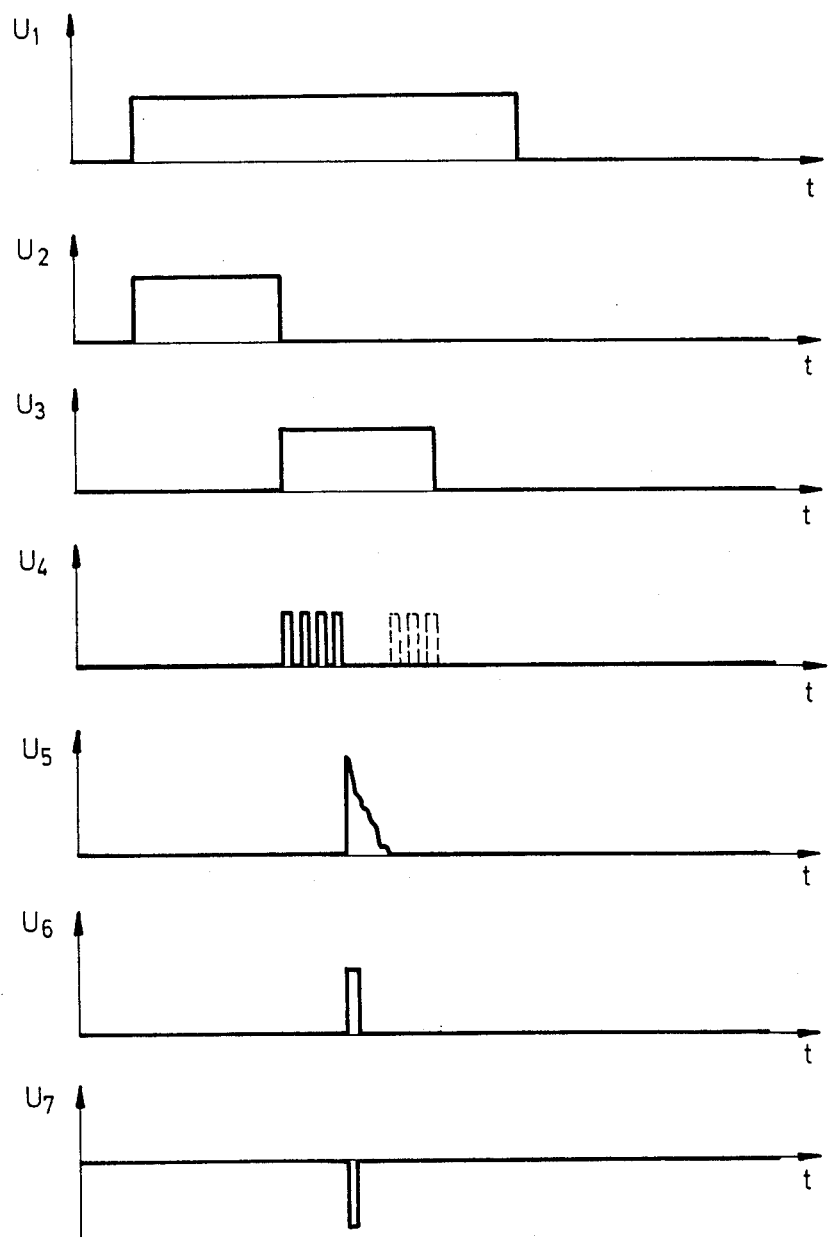
FIG. 2 is a graphical representation of the timewise cycles of the most important voltages encountered in the circuit diagram of FIG. 1.

With each output impulse $U_1$ of the transmission pulse generator 5, monostable flip-flop 7 further is displaced into its instable condition, which accordingly thereby generates an output impulse, corresponding to $U_2(t)$ pursuant to FIG. 2. At the end of this impulse $U_2$, the monostable trigger flip-flop 8 is contacted, which then generates an output impulse $U_3(t)$ pursuant to FIG. 2. The time intervals of instability of both monostable triggers or flip-flops 7 and 8 is thereby so selected and correlated with respect to each other, that the output impulse $U_3$ of the flip-flop 8 occurs just during such a time period in which the ultrasonic wave emitted from the ultrasonic head 1 passes through a predetermined skull distance which is to be examined. Preferably, the output impulse $U_3$ of the monostable flip-flop 8 limits the examination width within the brain-containing portion of the skull to values in the range of between 60mm to 200mm.

The output impulse $U_3$ of the monostable flip-flop 8 now, on one side, displaces the heretofore closed electronic gate 22 into an opened condition for the duration of the impulses $U_3$. An ultrasonic impulse which is received by the receiver 6 during the open time period for the gate 22, thereby can pass through the gate 22 without any hindrance. With the commencement of the impulses $U_3$ of the flip-flop 8, on the other side there is, however, also activated the pulse generator 9, which counts impulses $U_4(t)$ at a high frequency (2MHz) into the impulse counter 10. The counting in of these impulses into the counter 10 thereby occurs for so long until ultrasonic impulse projected by the ultrasonic head 1 impinges against the ultrasonic head 2. The output impulse $U_5(t)$ of the receiving amplifier 6, which is generated at that instance, now switches the storage 11 through the opened electronic gate 22 (after amplification in amplifier 24), as well as through the Schmitt-trigger 23 ($U_6(t)$, in such as sense, that the storage abruptly assumes and stores the counting condition of the counter 10 accumulated up to the occurrence timepoint of the received impulses. Concurrently, the comparator 12 also detects the counting balance between the counter 10 and storage 11 and generates for the first time at its output 13 a marking impulse $U_7$ for the position of the theoretical median echo.

Subsequently, there commences the actual formation of the ultrasonic-echo encephalograph in a reflection operation. For this purpose, the switch 3 is switched over into the phantom-illustrated switching position. The ultrasonic head 1 is then removed from the skull, and the ultrasonic head 2 now operates selectively as an ultrasonic transmitter and echo-impulse receiver. At each occurrence of a transmission pulse impulse $U_1$, by means of the monostable triggers or flip-flops 7 and 8, the counter 9 is newly started, and thereby the counter 10 increases its count within each transmission-receiving period. Respectively, at the instance in which the counting condition of the counter 10 corresponds to the stored value of the storage 11, the comparator 12 again generates its output impulse $U_7$. Periodically, in synchronism with the ultrasonic radiation, there is accordingly generated a marking impulse $U_7$ for the theoretical median echo, whereby the generation is effected in a delayed manner by the extent of the measured transit time of the ultrasonics during the sounding through the skull as contrasted with the output impulse $U_3$ of the monostable trigger or flip-flop 8.

Through the selective switching of the selector switch 15 between the track of the echo impulses and the track of the marking impulses, there is thus formed on the picture screen of the electron-beam tube 17, the desired echo image (echo-encephalograph), together with the blended-in marking impulse which represents the position of the theoretical median echo. The tracks of the echo impulses, as well as those of the marking impulses, thereby may represent the same zero or base line. By means of the superposition with different direct potentials through the direct or constant potential generator 14, and respectively 19, the zero or base lines, however, may be displaced with respect to each other. Correspondingly, on the picture screen of the tube 17, the marking impulse which is shown pursuant to FIG. 1 with a negative polarity, may also indicate a positive polarity.

While there has been shown what is considered to be the preferred embodiment of the invention, it will be obvious that modifications may be made which come within the scope of the disclosure of the specification.

What is claimed is:

1. In an arrangement for the ultrasonic echo encephalography of a patient's skull, including at least two ultrasonic heads for providing the theoretical median echo, switching means (3) having a first switching condition providing for sounding operation between a first head (1) at one side of a patients skull and a second head (2) at the opposite side of the patient's skull, and having a second switching condition providing for reflection operation, ultrasonic pulse means (5, 4) connected to the first head (1) in said first switching condition of said switching means (3) for energizing said first head (1) to transmit an ultrasonic pulse toward the second head (2), receiving means (6, 22, 24, 23) coupled to the second head (2) in the first switching condition for receiving the output of the second head (2) and for generating an output pulse ($U_6$) representing the timepoint of receipt by the second head (2) of the ultrasonic pulse from the first head (1), time measurement means (9, 10) comprising an impulse generator (9) having an output for supplying periodic pulses, and impulse counter means (10)

having an input connected to the output of said impulse generator (9) and operable in both said first and second switching conditions for counting said periodic pulses, timing means (7, 8) coupled with said pulse means (5) and with said time measurement means (9, 10) and responsive to the energization of the first head (1) by said pulse means (5, 4) in said first switching condition to actuate said time measurement means (9, 10) so that the impulse counter means (10) counts the periodic pulses from the impulse generator (9), storage means (11) coupled with said counter means (10) and responsive to the output pulse ($U_6$) from said receiving means (6, 22, 24, 23) to store a count equal to the counting position of said counter means (10) at the timepoint of receipt by the second head (2) of the ultrasonic pulse from the first head (1), a count condition comparator (12) connected to the counter means (10) and to storage means (11) and being operable in the second switching condition of the switching means (3) to periodically compare the count of said counter means (10) with the stored count of said storage means (11) so as to deliver an output signal ($U_7$) at the balance of both count conditions, display means (17) for receiving echo signals from one of the heads in the second switching condition, said timing means (7, 8) being operative to initiate counting of said counter means (10) in each cycle of energization of one of the head during reflection operation, and means (14, 15) operable in the second switching condition for periodically connecting the output of the count condition comparator (12) with the display means (17) for supplying a marking signal ($U_7$) to the display means (17) each time the counter means (10) reaches a count equal to the stored count of said storage means (11) during reflection operation.

2. An arrangement as claimed in claim 1, said timing means (7, 8) comprising a monostable flip-flop (8) generating an output impulse ($U_3$) in the unstable condition thereof for starting said pulse generator (9) at the entry of the ultrasonics into the skull examination region.

3. An arrangement as claimed in claim 2, said timing means (7, 8) comprising a second monostable flip-flop (7) adapted to be periodically displaced into an unstable condition by the initiation of ultrasonic radiation, said second flip-flop (7) actuating said first-mentioned monostable flip-flop (8) upon being returned into the stable condition thereof.

4. An arrangement as claimed in claim 3, said first and second monostable flip-flops (8, 7) having unstable time periods selected and mutually interrelated so that the beginning and the end of the output impulses of said first flip-flop (8) determine, respectively, the timepoints of the ultrasonics entry and substantially the ultrasonics egress from the examined skull portion.

5. An arrangement as claimed in claim 4, said first flip-flop (8) being adjustable so as to have the output impulses ($U_3$) thereof limit the examination width in the brain-containing skull portion to values in the range of between 60 mm to 200 mm.

6. An arrangement as claimed in claim 3, said storage means (11) being activated through the received ultrasonic signal for assuming the count condition of said inpulse counter means (10) accumulated during sounding measurement at the instant of the transmitted sound being received by said second ultrasonic head (2).

7. An arrangement as claimed in claim 6, said receiving means (6, 22, 24, 23) comprising a Schmitt-trigger (23) for activating said storage means (11) through the ultrasonic receiving signal for assuming the count condition of said counter means (10).

8. An arrangement as claimed in claim 7, said receiving means (6, 22, 24, 23) comprising an electronic gate (22) connected preceding said Schmitt-trigger (23) and said storage means (11), said gate (22) being opened by said first flip-flop (8) at the beginning of the unstable phase thereof for conducting the received ultrasonic signals to said storage means (11) and Schmitt-trigger (23), and closed at the end of the unstable phase of said flip-flop (8).

9. An arrangement as claimed in claim 8, said receiving means (6, 22, 24, 23) comprising an amplifier (24) for the ultrasonic signals passed through by said electronic gate (22), and regulating means (25) for regulating the degree of amplification of a receiving amplifier (6) to higher or lower values dependent upon the amplitude of the output signals of the receiving amplifier (6) and of said first-mentioned amplifier (24).

10. An arrangement as claimed in claim 1, said counter means (10) comprising a digital counter, and said storage means (11) comprising a digital storage.

11. An arrangement as claimed 10, said digital storage (11) being a storage flip-flop.

12. An arrangement as claimed in claim 10, said comparator (12) being a digital comparator adapted to directly compare the digitally-appearing count conditions of said digital counter (10) and of said digital storage (11).

* * * * *